United States Patent [19]

Culmo

[11] 4,400,354

[45] Aug. 23, 1983

[54] APPARATUS USEFUL FOR ANALYZING REFRACTORY SUBSTANCES

[75] Inventor: Robert F. Culmo, Woodbridge, Conn.

[73] Assignee: The Perkin-Elmer Corporation, Norwalk, Conn.

[21] Appl. No.: 235,781

[22] Filed: Feb. 19, 1981

[51] Int. Cl.³ .......................................... G01N 31/12
[52] U.S. Cl. ..................................... 422/78; 422/80; 436/155; 436/159; 436/160
[58] Field of Search ............... 23/230 PC; 422/78, 80; 423/592; 436/155, 159, 160

[56] References Cited

U.S. PATENT DOCUMENTS

| | | | |
|---|---|---|---|
| 3,671,195 | 6/1972 | Bersin | 23/230 PC |
| 3,726,646 | 4/1973 | Kravetz et al. | 23/230 PC |
| 4,098,576 | 7/1978 | Judge | 23/230 PC |
| 4,282,183 | 8/1981 | Bredeweg et al. | 422/78 |

FOREIGN PATENT DOCUMENTS 650158  10/1962  Canada .................................. 422/80

Primary Examiner—Herbert T. Carter
Attorney, Agent, or Firm—S. A. Giarratana; F. L. Masselle; R. A. Hays

[57] ABSTRACT

An apparatus and method useful for analyzing refractory substances includes a means for locally heating a sample portion of a refractory material to generate the dissociated vapor thereof.

7 Claims, 2 Drawing Figures

U.S. Patent  Aug. 23, 1983  4,400,354
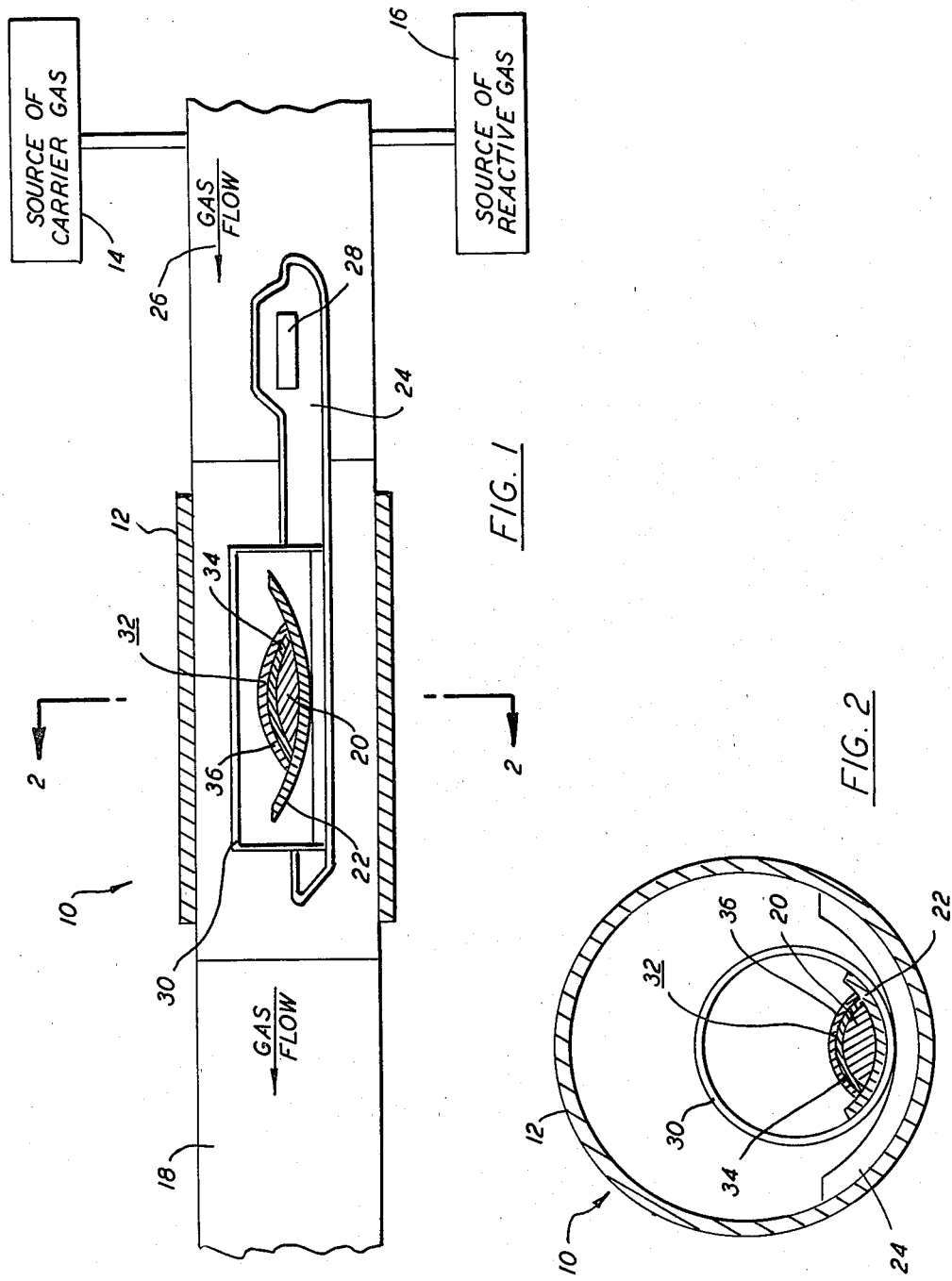

APPARATUS USEFUL FOR ANALYZING REFRACTORY SUBSTANCES

BACKGROUND OF THE INVENTION

The present invention generally relates to the elemental analysis of samples and, in particular, relates to an apparatus and method useful for analyzing refractory substances.

One conventional class of the elemental analysis of unknown samples includes the oxidation of the sample under test and thereafter conveying the sample gas to a measuring cell. A particularly difficult group of materials to so analyze are those materials known as refractory substances. The difficulty lies in the fact that refractory substances are stable in the solid state at rather high temperatures.

At present, conventional instruments for analyzing refractory substances employ an induction furnace to achieve the necessary temperatures for oxidizing such substances. In general, the furnaces presently used for refractory material analysis are designed to reach temperatures on the order of about 2000° C. While effective for the intended purpose, such instruments are also large, expensive and require elaborate interconnections for processing the sample gas. Additionally, such instruments are usually restricted only to the analysis of refractory substances and are quite ineffective for analyzing substances which melt or oxidize at much lower temperatures.

There is thence a need for a single instrument capable of analyzing both non-refractory substances and refractory substances without undue expense or loss of efficiency.

SUMMARY OF THE INVENTION

Accordingly, it is one object of the present invention to provide an apparatus useful for analyzing refractory substances, which apparatus being adaptable to conventional elemental analyzers.

This object is accomplished, at least in part, by an apparatus which includes a means for locally increasing the temperature of the sample under test.

Other objects and advantages will become apparent from the following detailed description and appended drawing.

BRIEF DESCRIPTION OF THE DRAWING

FIG. 1 is a partial cross-sectional view, not drawn to scale, of an apparatus embodying the principles of the present invention.

FIG. 2 is a partial cross-sectional view of the apparatus shown in FIG. 1 taken along the line 2—2 thereof.

DETAILED DESCRIPTION OF THE INVENTION

An elemental analyzer, generally indicated at 10 in the drawing includes a furnace 12, a source of inert carrier gas 14, a source of reactive gas 16 and an analytical cell 18.

As known in the art, a typical analysis of a sample is performed by weighing out a portion 20 of the sample and placing that portion 20 in a sample vessel 22. The vessel 22 is ordinarily platinum or some other material characterized as being stable and inert at relatively high temperatures, i.e. on the order of about 1000° C. The vessel 22 is then placed in a quartz ladle 24 which is used to convey the vessel 22 from the sample entrance tube 26 into the furnace 12. As shown in FIG. 1, the sample tube 26 extends completely through the furnace 12 to the analytical cell 18. Preferably, the conveyance is accomplished by moving a magnet (not shown) externally along the entrance tube 26 which, by the presence of a magnetic slug 28 in one end of the quartz ladle 24, moves the ladle 24 into the desired position.

Once the ladle 24 is in place, the furnace 12 is activated to heat the sample portion 20 to a desired sample oxidation temperature, usually the upper temperature limit of conventional elemental analysis instruments is on the order of about 1000° C. During the heating, an inert carrier gas is made to flow through the furnace 12 whereby the sample gas is carried into an analytical cell 18.

The apparatus and procedure discussed above are substantially useless if a sample of, for example, silicon carbide is to be analyzed. That is, silicon carbide sublimes, i.e. exhibits a phase state transition from solid to vapor without going through a liquid state, at a temperature of about 2200° C. Further, even after the silicon carbide is sublimated, it must still be dissociated, i.e. the silicon and carbon atoms separated, in order to be analyzed. Since such dissociation takes place at between 3000° C. and 4000° C., the above-discussed apparatus and procedure is clearly inadequate. The inadequacy arises not only from the upper limit of the conventional furnace, i.e. about 1000° C., but also from the fact that the quartz ladle 24 tends to soften at an elevated temperature of about 1100° or 1200° C.

The apparatus 10 shown in FIG. 1 also includes a heat containment member 30 and a means 32 for locally increasing the temperature of the sample portion 20. As used herein, the terms "local", "localized" or "locally" when used in reference to increasing the temperature of the sample portion 20 means that the heating is in situ, i.e. concentrated in or around the sample portion 20 only. The heat containment member 30 is, in the preferred embodiment, a cylindrical ceramic tube, i.e., a hollow cylinder. The member 30 can be constructed from pure alumina ($Al_2O_3$), zirconium oxide, or the like and serves not only to contain the local heat generated by the means 32 but also serves to protect the ladle 24 and furnace 12 from the locally created high temperatures. The means 32 for locally increasing the temperature of the sample portion 20 is, preferably, at least one layer of metal powder which can enter into an exothermic chemical reaction. In one instance, a single layer of powdered tin, which can be initiated into an exothermic reaction at about 900° C., is distributed over the sample portion 20. In order to facilitate and accelerate the exothermic reaction, thus generating localized heating of the sample portion 20, caused by the heat of formation of tin oxide, an oxygen gas flow of about 4 to 6 liters/minute, preferably about 5 liters/minute, is supplied through the member 30 from the source of reactive gas 16. Thus, the cylindrical shape of the member 30 is particularly advantageous to assist in concentrating the oxygen gas flow across the sample portion 20.

As one alternative to utilizing a means 32 having only a single layer of powdered tin, a means 32 having more than one powdered metal can be used. In such an instance, it is preferred, a first layer 34 of powdered aluminum is distributed over the sample portion 20 and a second layer 34 of powdered tin is distributed over the first layer 34. It has been determined that when powdered aluminum is employed, the aluminum powder should be stored in an inert, or non-oxidizing, environment to prevent the formation of aluminum oxide therein which would subsequently severely reduce the effectiveness of the aluminum powder in any exothermic reaction. An alternative to the use of powdered aluminum is the use of powdered magnesium. Advantageously, powdered magnesium does not oxidize as readily as aluminum and thus storage is not a major consideration.

In any event, the utilization of a means 32 substantially necessitates the use of an aluminum sample vessel 22 rather than the usual platinum vessel. The change of material is preferably first because at the locally increased temperature the vessel 22 is effectively destroyed. It is, of course, readily recognized that it is considerably less expensive to replace aluminum vessels than platinum vessels. Further, and to a much lesser degree of consideration by using aluminum, the material of the vessel 22 can enter into the exothermic reaction.

As a specific example, a sample portion 20, of between 1 and 5 milligrams, of silicon carbide is accurately weighed and placed into an aluminum sample vessel 22. Then, about 100 to 150 milligrams of powdered tin, or alternatively about 50 milligrams of powdered aluminum and about 50 milligrams of powdered tin, is distributed over the sample portion 20. In the case where the aluminum/tin combination is used, the aluminum powder should be distributed over the sample portion 20 first and the tin powder distributed over the aluminum powder. In any event, each layer should completely cover the sample portion 20. The amount of sample portion 20 will, of course, vary depending upon the substance being analyzed.

The sample vessel 22 is next placed inside the ceramic tube 30 which is loaded onto the quartz ladle 24. It should be noted that a conventional quartz ladle can readily be modified to accept the tube 30. Such modification can be accomplished according to techniques known in the machining art.

The ladle 24 is then moved inside the furnace 12 which is next heated in the conventional fashion. It is immaterial to the present method whether the sample portion 20 is injected into a preheated furnace or if the furnace is heated after the sample portion 20 is introduced thereinto. As noted above, a flow of oxygen must be provided to not only facilitate, but also accelerate the exothermic reaction. The desired flow can be achieved in conventional instruments by providing oxygen from a source which has a pressure of between about 50 to 60 p.s.i. The dissociated gases generated and substantially simultaneously oxidized from the above-described method are analyzed in the normal fashion.

Although the present invention has been described herein by use of specific example, additional arrangements and modifications will become apparent therefrom. Hence, this description is intended to be illustrative and not limiting. Thus, the present invention is considered limited only by the appended claims and the reasonable interpretation and extensions thereof.

What is claimed is:

1. In combination with a non-refractory sample elemental analyzer, including a furnace having an upper temperature limit capable of oxidizing only non-refractory materials having a sample delivery tube extending therethrough, an apparatus for oxidizing a refractory sample; said apparatus comprising:
   an open, hollow, cylindrical heat containment member having said refractory sample therein, said member being within said sample delivery tube positioned within said furnace of said analyzer; and
   a layer of powdered material overlying said refractory sample, said powdered material being exothermically reactive at a temperature less than said upper limit of said furnace, whereby when said powdered material exothermically reacts, the temperature limit available for oxidizing said refractory sample is extended such that said refractory sample is vaporized.

2. Apparatus as claimed in claim 1 further comprising:
   means for accelerating the exothermic reaction.

3. Apparatus as claimed in claim 2 wherein said accelerating means is oxygen gas.

4. Apparatus as claimed in claim 3 wherein said oxygen gas flows at a rate of between 4 to 6 liters/minute.

5. Apparatus as claimed in claim 1 further comprising:
   a sample vessel for holding said refractory sample, said sample being within said heat containment member.

6. Apparatus as claimed in claim 1 wherein said layer of powdered material overlies a layer of powdered aluminum.

7. Apparatus as claimed in claim 1 wherein said furnace has an upper temperature limit on the order of about 1000° C.

* * * * *